(12) United States Patent
Kaiser

(10) Patent No.: US 7,862,769 B2
(45) Date of Patent: Jan. 4, 2011

(54) TESTING BODY, PARTICULARLY FOR VERIFYING THE PENETRATION PROPERTIES OF A STERILIZING AGENT IN STERILIZATION PROCESSES

(75) Inventor: Ulrich Kaiser, Feldstrasse 14, Glashuetten (DE) 61479

(73) Assignee: Ulrich Kaiser, Glashuetten (DE)

( * ) Notice: Subject to any disclaimer, the term of this patent is extended or adjusted under 35 U.S.C. 154(b) by 942 days.

(21) Appl. No.: 10/551,146

(22) PCT Filed: Mar. 26, 2004

(86) PCT No.: PCT/EP2004/003198

§ 371 (c)(1),
(2), (4) Date: Oct. 31, 2006

(87) PCT Pub. No.: WO2004/084956

PCT Pub. Date: Oct. 7, 2004

(65) Prior Publication Data
US 2007/0178549 A1    Aug. 2, 2007

(30) Foreign Application Priority Data
Mar. 28, 2003  (EP) .................... 03007122

(51) Int. Cl.
*G01N 33/12* (2006.01)
(52) U.S. Cl. ................ 422/58; 422/61; 436/1; 436/164

(58) Field of Classification Search ............ 436/1, 436/166, 164; 422/58, 61
See application file for complete search history.

(56) References Cited

U.S. PATENT DOCUMENTS 5,872,004 A    2/1999   Bolsen ............ 435/287.4

FOREIGN PATENT DOCUMENTS

| DE | 87 00 471 U | 1/1987 |
|---|---|---|
| DE | 298 11 381 U | 11/1998 |
| EP | 0 628 814 | 12/1994 |
| EP | 0 982 039 B1 | 3/2000 |
| EP | 1 084 714 A1 | 3/2001 |
| EP | 1 172 117 A2 | 1/2002 |
| EP | 0 882 456 B1 | 3/2003 |
| WO | WO 97/12637 | 4/1997 |

*Primary Examiner*—Lyle A Alexander
(74) *Attorney, Agent, or Firm*—Leydig, Voit & Mayer, Ltd.

(57) ABSTRACT

A testing body (1) that is provided for verifying the penetration properties of a sterilization agent has, with a compact design, a particularly high detection sensitivity and is thus particularly well-suited or use in the sterilization of minimally invasive surgical instruments that are known to be difficult to remove air therefrom thereby rendering the sterilization thereof problematic. For this purpose, the testing body (1) has a detector volume (24), which is provided for accommodating an indicator (26) and which can be connected to a sterilization chamber via a gas collecting space (4). According to the invention, the gas collecting space (4) has a multi-stage design, and the cross-section and the volume of each stage (14, 16) decrease between adjacent stages (14, 16) in the direction of the detector volume (24).

13 Claims, 3 Drawing Sheets

TESTING BODY, PARTICULARLY FOR VERIFYING THE PENETRATION PROPERTIES OF A STERILIZING AGENT IN STERILIZATION PROCESSES

FIELD OF THE INVENTION

The invention refers to a test device, especially to check the penetration characteristics of a sterilization agent, in which the detector volume intended to host an indicator is connected with a sterilization chamber via a gas collection volume for the reception of an indicator. It further concerns the use of such a test device. Such test devices for example are known from EP 0 628 814 A1 or from EP 1 172 117 A2.

BACKGROUND

For aseptic applications like operations in hospitals the use of sterile tools, instruments or materials is absolutely necessary. At a therefore necessary sterilization the sterilizing agent, for example steam, formaldehyde, ethylene oxide, hydrogen peroxide and/or ozone, is usually transferred via the gas phase to the surface of the instrument to be sterilized, to assure the total kill of existing germs. For this purpose sterilizers with sterilization chambers are normally used, in which the instruments or materials—normally packaged—which have to be sterilized, are put in. For the real sterilization the sterilization chamber is flooded with gaseous sterilant—also named sterilizing agent—, which requires that the air atmosphere inside has to be removed before. The sterilization agent shall contact the surfaces of the instruments or materials to be sterilized so that the desired kill of the germs occurs.

As the complete sterilization of the goods at all surface areas is only guaranteed if the sterilization agent reaches all interior surfaces as well, for example porous goods or hollow devices, the removal of the air inside the goods and inside the sterilization room has to be secured by a suitable air removal procedure at the beginning of the sterilization process. After that the sterilization chamber is flooded with the sterilization agent in order to reach all surfaces of the devices inside the sterilization chamber with the sterilization agent. This is only possible when the complete penetration of the sterilization agent is assured to all surfaces.

The complex structure of medical instruments is known to be problematic in sterilization processes. More and more medical devices are used with relatively long pipes or tubes and comparatively small free cross sections, so that a reliable surface contact of the sterilization agent to all interior surfaces is made more difficult, if there are other gases present. Furthermore materials and goods with complex interior surfaces, for example textile packages, require sterilization. In such cases existing accumulations of remaining air or other non condensable gases (NCG) may prevent complete or part contact of those surfaces. However the complete sterilization is only assured when the air inside the goods is completely removed before the sterilization process, and/or, when during the vacuum stage no air enters through leaks and/or no NCG are introduced into the sterilization chamber with the sterilization agent, to assure, that the sterilization agent can reach all surfaces.

As sterility of instruments cannot be tested directly before use, the validation of sterilization processes after start up and routine monitoring during the sterilization process are necessary. In addition detectors are used, to prove the success of the sterilization process. For example chemical indicators are used which change their colour when their surfaces are covered by the sterilization agent, for example with steam, so that it is recognizable that the chemical indicator has been contacted directly. Alternatively or additionally biological indicators may be used in form of stripes, suspensions or self-contained germ cultures or mixtures of different germ cultures. After the end of a sterilization process it is tested, if all germs have been completely inactivated.

The use of such indicators demonstrates, if an active coverage of the indicator surface with sterilization agent has occurred at the place, where the indicator inside the sterilization chamber is positioned. Using such indicators is no direct proof of the sterilization success at comparatively inaccessible surfaces of complex instruments, because the indicators cannot be placed at those critical areas. Therefore special test devices are sterilized together with the goods which have to be treated, to determine the success of the sterilization. For example, for the sterilization process of textiles or other materials, from Bowie and Dick a standard test pack was described (Bowie, I. W., e.a., The Bowie+Dick autoclave tape test, Lancet I, 1963, p. 585-587), in which a chemical indicator test sheet of DIN A4-size has been placed centrally in a cotton package of 6.6 kg weight. Though this standard test is not exactly reproducible because of the cotton quality, cotton history and individuality of the packages, and its penetration characteristic is different from a hollow device.

Alternatively so called test devices or test device systems can be used. In such a test device system, as described for example in EP 0 628 814 A1 or in EN 867-5, the difficult accessible inside surface of complex instruments is simulated by a suitable model, enabling to monitor the success of the penetration processes into complex instruments in an analogous way.

Those well-known test device systems, also named "process challenge device" (PCD), consist of a suitable detector to approve the contact to the sterilization agent, connected to a suitably chosen length of tube at the gas entering side, which is open at its admission end. This hollow device system simulates the penetration characteristics of similarly designed instruments which are supposed to be sterilized, where especially during an alternate gas exchange according a fractionated vacuum and/or the condensation of steam eventually remaining air or other non-condensable gases at the tube end in the area of the detector are concentrated. So the tube works as a gas-collection-volume for remaining air or other non condensable gases to though the detector is connected to the sterilization chamber via this gas-collection-volume.

If the detector of such a system, connected to the tube end, detects sterilization agent, it can be assumed, that—adding a security supplement according to the Penetration characteristics—the instruments most inaccessible points of their inner surfaces must have been in contact with sterilization agent as well. Such a tube model as a test device which can hold for example biological or chemical indicators as a detector is also intended for the verification of sterilization processes in Euro Standard EN 867-5. To check the sterilization success of more complex goods, test devices of a different construction which are in their dimension suitably adapted, can be used, as described for example in the Euro Standards EN 285, EN 14180, EN 1422 or EN 867-5.

The use of such test devices makes it also possible to use physical test methods under specific conditions. For example from EP 1 172 117 A2 a sterilization test system is known, in which the local change of temperature occurring by the condensation of steam is detected at the place to be monitored as a proof for an occurred contact of an inside surface by the sterilization agent. The test device used in that system is particularly suitable designed regarding to its heat conducting properties.

However the available measure accuracy of these systems is limited. Especially at the modelling of comparably complex or for the sterilization agent hardly accessible instruments the required measure sensitivity is—if at all—only achievable if a comparably voluminous gas-collection-volume is used. Using a tube material to form the gas-collection-volume, heat transfer through the tube wall can appear and may give false results, if thermoelectric measurements are used as detectors.

SUMMARY OF THE INVENTION

It is an object of the invention to design a test device of the above mentioned type, to achieve a very high sensitivity with a compact construction.

The object of the invention is achieved, for example, by using multi-stage gas-collection-volume, in which the cross section and the volume of every stage decrease towards the direction of the detector.

The invention emanates from the consideration that common test devices only achieve a high sensitivity with an adequate long dimensioned gas-collection-volume, at the cost of the compactness. Furthermore disadvantageous is the condensation of steam in steam sterilization processes in long thin tubes. For a compact construction using common indicators, like for example physical methods, biological or chemical indicators, the gas feeding to the detector volume should be designed in a way, that the segregation of remaining air or other non condensable gases in the sterilization agent is achieved using bigger volumes and those are transferred over the decrease of the cross section to the detector. Such an amplification is achievable by an intentional concentration of air or remaining gases directed towards the detector volume. Therefore the gas-collection-volume of the test device is at least double-stage, but if necessary even multi-stage constructed at which the stages regarding to their particular volume and/or cross section differ from each other. The stage, which is directly neighbouring the detector volume, can thereby serve to simulate the penetration of particularly inaccessible inner surfaces of the instruments, which have to be treated. The concentration of remaining air in this stage, directly neighbouring the detector volume, enhances a high sensitivity using further stages of the gas-collection-volume towards the direction of the sterilization chamber, which serve as the condensation zone for the selective condensation of the sterilization agent, if steam sterilization processes are used.

For an especially high efficacy of the selective concentration of still remaining air in those stages of the gas-collection-volume and therefore an especially high sensitivity, the cross section between neighbouring stages decreases advantageously towards the direction of the detector volume at least by 50%, better by more than 75%. Consequently in the test device a gas current path, starting at internal volume of the sterilization chamber is connected to first streaming volume stage with a comparably big volume and cross section, via the decreasing volume and cross section in the second streaming volume stage to the detector. A further advantageous design is, to make the volume of the stage towards the detector smaller than the volume of the stage towards the sterilization chamber. The streaming channel for the gas inside the test device in front of the detector is a series connection of a wide and a narrow channel.

To achieve an especial sensitivity, the detector in the gas-collection-volume is advantageously designed this way, that the existence of even marginal amounts of remaining air will prevent the admission of the sterilization agent. Especially at an operational mode with alternating media as a consequence of the gas exchange still remaining amounts of air accumulate to the end area of the probe channel, the detector is necessarily placed in an area at the opposite end of the gas-collection-volume-port.

The test device can be adopted regarding to the dimension of its essential elements to specified standardised test processes or real goods to be treated. For this purpose the cross section of the gas-collection-volume stage directly neighbouring the detector volume is advantageously about 1 to 20 $mm^2$, at which the gas-collection-volume in this stage in further or alternative design has a channel length of at least 10 cm, preferably of about 30 to 100 cm. The stages of the gas-collection-volume can show a suitable cross section form, especially a round or square cross section, and are made in each case of a metal- or plastic-pipe or box, so that in comparison to tubes a high stability and good durability results.

A very compact design is achievable, when a first stage of the gas-collection-volume in the manner of an interleaved design is arranged essentially inside the second stage of the gas-collection-volume. The second stage of the gas-collection-volume is thereby in a further advantageous design as the first stage surrounding outside case, so that the stage of the gas-collection-volume neighbouring the detector volume is led inside the outside case. The outside case can be designed as any hollow space, which is provided with suitably placed holes so that the gas side is connected with the sterilization chamber.

An alternative advantageous design as a compact construction is also in this way achievable that a first stage of the gas-collection-volume is advantageously constructed around or in a further stage of the gas-collection-volume forming an outside case, at which the first stage especially can wind around or in the outside case like a helix.

Alternatively the gas-collection-volume can be adopted inside to further requirements regarding its flow characteristics. Therefore the gas-collection-volume advantageously is in at least one stage filled with a porous material, at which as porous material especially cellulose, cotton, glass wool, mineral wool or metal wool can be chosen. The porous material is thereby advantageously arranged especially inside an as outside case designed stage of the gas-collection-volume, in order to hold the convection in the gas-collection-volume as low as possible and to avoid back mixtures.

Advantageously the detector of the test device itself is designed to achieve an especially high sensitivity. For that purpose the detector contains an indicator, which is arranged in the detector volume, and is connected to the probe channel at the gas side. The detector volume is thereby primarily very low and extensively adapted to the volume that is taken by the actual indicator. Advantageously the detector volume is chosen smaller than about 250-500 µl, so that at the use of a common chemical or biological indicator with paper as carrier, consuming a volume of 100-250 µl, nearly half of the detector volume is filled up with the actual indicator. Thereby primarily the stages of the gas-collection-volume as well as the detector are made of metal or plastic or of a metal-plastic-construction, with adapted, different wall thicknesses.

As detector a system for the evaluation of physical parameters can be used, like for example a sensor for moisture, temperature, pressure and/or an ultrasonic sensor, which is located in a sterilization chamber, and may be designed also as a so-called data logger for wireless transmission of the received data. Solid materials like for example salts can be used as well, which change physically when the sterilization agent is present, so for example achieve their melting point and/or change their colour. Advantageous a chemical indicator is used as indicator, which changes its colour when in contact with the used sterilization agent, or a biological indicator, for example in the form of indicator stripes and/or self-developed biological indicators.

The test device is especially suitable monitoring sterilization processes with gaseous sterilization agents like for example low-temperature steam-formaldehyde-, ethylene oxide-, hydrogen peroxide- or ozone-sterilization-processes. The series gas-connection of several stages of the gas-collection-volume before the detector achieves specific current properties and the presence of a condensation area makes the test device also notably suitable, to allow specific condensation of the sterilization agent for the use in a sterilization process in which steam is used as the sterilization agent. Advantageous the test device is therefore used to monitor steam sterilization processes. Basically all air removal versions for the sterilization chamber may be used. The test device in the process informs the operator, which steam penetration characteristics the process provides.

The advantages achieved by the invention primarily consist therein, of the gas side series connexion of several stages of the gas-collection-volume with different dimensions, especially using steam as the sterilization agent, a condensation area for the selective local condensation of sterilization agent is provided, which leads to a local concentration of remaining air and/or non condensable gases in the area of stage of the gas-collection-volume neighbouring the detector volume. To achieve an evaluation of cumulative amounts of remaining air and/or non condensable gases, particularly during changing evacuation and new admission of steam in the form of an integral system, assures an amplifying effect during the detection. Therefore, the remaining air stays in the port area of the gas-collection-volume also during pressure reduction in the sterilization chamber, without affecting eventually appearing convections or other currents in the sterilization chamber. With the new pressurisation of the sterilization chamber with steam the remaining air in the gas-collection-volume—if present—is pressurized again in the stage directly neighbouring and reaching the detector. Thus also very mean amounts of remaining air are systematically led into the verification area of the detector so that the sensitivity to remaining air is especially high. The surface coverage of the indicator inside the detector with sterilization agent happens only, if in all other comparably complex hollow devices a reliable sterilization occurs.

Using the so achieved amplifying effect, a high verification sensitivity can be assured with a compact design, using especially robust and non-aging materials for the gas-collection-volume. The achieved amplifying effect is so high, that only instruments which are very hard to penetrate like for example trocars, arthroscopy-instruments or multi-channel endoscopes can be reliable simulated using a compact design. Because of the multi-stage-design there are several alternative degrees of freedom for the simulation of real instruments possible, so that porous or hollow device constructions can be simulated as well.

BRIEF DESCRIPTION OF THE DRAWINGS

An exemplary embodiment of the present invention is explained in greater detail on the basis of a drawings in which.

DETAILED DESCRIPTION

Figure 1:
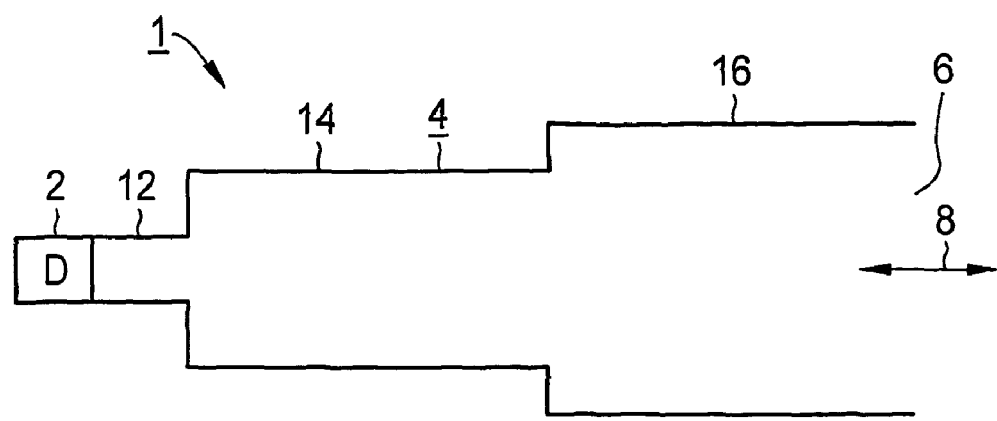
FIG. 1 shows a construction scheme for a test device, and
FIGS. 2 to 5 each show a test device for the verification of the penetration characteristics of a sterilization agent.

The test device 1 displayed in FIG. 1 shows a construction scheme designed to test the penetration characteristics of a sterilization agent. The knowledge achieved during the use of the test device 1 may be used especially for the verification or testing steam in a sterilization process. Using such a steam sterilization process the instruments or materials to be sterilized are put into a sterilization chamber not specified. At first the sterilization chamber is removed from air. The air removal process can be carried out by a downward gravity displacement process, super- or sub-atmospheric air removal cycles or their combinations.

In order to prove such an air removal process, based on a fractionated vacuum, where the instruments and materials are sterilized, really all inner surfaces are covered by the sterilization agent and therefore the complete penetration has necessarily occurred. The test device 1 is put in the sterilization chamber as well, for example for the validation of the sterilization procedure at start-up or for routine monitoring during the sterilization processes. The test device 1 includes a detector 2, which is designed for the direct prove that a surface coverage by the sterilization agent has occurred effectively.

The test device 1 is designed to simulate the proper surface coverage of comparably hardly accessible internal surfaces of instruments or materials. Therefore a gas-collection-volume 4 is connected with the detector 2, whose end port 6 is open, so that the detector 2, as indicated by the double arrow, is connected at the gas side to the sterilization chamber by the gas-collection-volume 4. The test device 1 is designed for an especially compact construction to achieve an especially high verification sensitivity regarding the penetration characteristics of the simulated instruments or devices at the same time. Therefore, the gas-collection-volume 4 is multi-stage-designed, for example a first stage 12 is directly neighbouring the detector 2 at the gas side and are connected in series with further stages 14, 16. Of course in addition of such a three stage construction further stages can be connected in series, or a dual stage construction may be intended.

The test device 1 is preferably designed for an application with especially high verification sensitivity, using a steam-based sterilization process in a sterilization chamber. Therefore the test device 1 is put into the sterilization chamber together with the instruments or materials to be sterilized. During the first step where the sterilization chamber is evacuated, the multi-stage-designed gas-collection-volume 4 is also evacuated. After that, when the sterilization chamber is filled with steam as sterilization agent, steam passes through the end port 6 into the third stage 16 and from there into the second and first stage 12, 14 of the gas-collection-volume 4. Still remaining air may prevent a reliable sterilization of the instruments or materials by the formation of air cushions pushed over the third stage 16 into the second and first stage 12, 14 of the gas-collection-volume 4 and concentrating at its end opposite of port 6. Therefore, the remaining air in the area of the detector 2 accumulates, so that a complete surface coverage of an indicator, placed in the detector, with steam, intended as sterilization agent does not occur.

In further successive occurring process steps, in which a fractionated vacuum with negative pressure is again created in the sterilization chamber and afterwards is filled with steam as sterilization agent, a successively increasing discharge of remaining air out of the sterilization chamber is achieved. Therefore an increasing reliable and universal surface coverage of all inner surfaces of the instruments is obtained which also analogously provides an increasingly better surface cover of the inner surface of the first stage 12 of the gas-collection-volume 4. If a sufficient penetration of the sterilization agent into the test device 1 occurs, also a total surface coverage of the indicator can be noticed. If this happens, the sterilization procedure is considered to be successful.

Using the multi-stage-design of the gas-collection-volume 4, connecting the second and third stage 14, 16 of the gas side, before the first stage 12 and selecting a suitably dimensioning of the stages 12, 14, 16 it is in the test device 1 secured, that for the process destructive remaining air in the direct area of the first stage 12, is specifically concentrated. This concentration occurs particularly by the preliminary stages 14, 16 at the gas side, which serves as condensation zone for the sterilization agent and provides a selective local condensation of the sterilization agent directly in front of the entrance area into the first stage 12. Because of the so achieved concentration of the remaining air or other non condensable gases, a sustainable and especial reliable proof of the remaining air or other non condensable gases occurs, so that the test device 1 can be used with an especial high proof precision.

Figure 2:
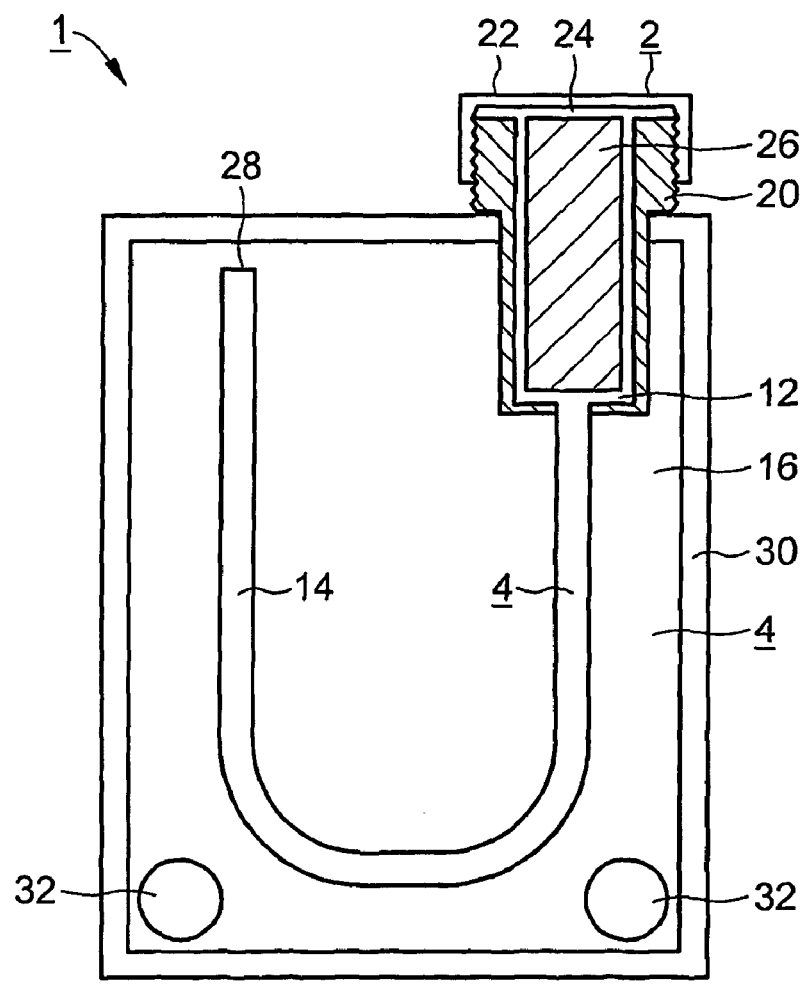

A test device, constructed according to the scheme in FIG. 1, is nested shown in FIG. 2. Its detector 2 contains a detector case 20 provided with a thread, which can be closed with a screwed cap 22. Inside the detector case 20 for example a detector volume 24 of about 240 µl is designed, in which an exchangeable indicator 26 is positioned.

The indicator 26, in that example has a volume of about 120 µl and is filling up the detector volume 24 approximately half, and could be designed as a sensor for the evaluation of a physical parameters, for example of the temperature or the pressure. The example however provides a biological or chemical indicator as indicator 26. The design using a biological indicator the indicator 26 is inoculated with germinable cultures at its surface, which are killed by a proper surface coverage with steam as sterilization agent. This design uses the indicator 26 to test for germs with the ability to reproduce after the sterilization has occurred. If germs with the ability to reproduce are found, the conclusion is drawn, that the sterilization was insufficient.

The indicator 26 when designed as a chemical indicator changes its colour when its surface is covered with steam as sterilization agent, so that by the visual monitoring the conclusion of a universal surface coverage can be drawn. If no surface coverage has occurred, the colour does not change or changes differently. The first stage 14 of the gas-collection-volume 4 is primarily formed of an elongated tube with a round or square cross section and preferentially made of metal or plastic. The example according to FIG. 2, consists of the first stage 14, directly neighbouring the detector 2, having an inside diameter of 2 mm, so that its internal cross section is about 3.2 mm². About 50 cm are chosen for the channel length. So the first stage 14 provides an inner volume of about 1.75 ml.

Here, the detector 2 for the gas is positioned at the end of the first stage 14 opposite the port 28. In that example, the first stage 14 u-shaped and therefore curved and is positioned inside a case 30 which surrounds the internal space of the second stage 16, so that a nested design results for the test device 1. The outside case 30 can be designed for example as a metal or plastic tube of about 20 cm length and 25 mm inside diameter, so that a volume of the second stage 16 of about 0.1 l results. Therefore the cross section and volume of the stages 14, 16 between the neighbouring stages 14, 16 significantly decrease towards the direction of the detector 2.

The second stage 16 connects at the gas side with the surrounding atmosphere over an amount of admittance openings 32 arranged in the outside case 30. Even at a tubular design of the outside case 30 its compact bottom area can be kept open for the creation of a comparably big dimensioned admittance opening 32. The port 28, connected over the first stage 14 at the gas side with the inside volume of the outside case 30, which forms the second stage 16 of the gas-collection-volume 4, is arranged inside the outside case 30 at a position at which with regard to the positioning of the admittance openings 32 also at gas exchanges only marginal gas streaming intensities can be assumed, so that the desired local concentration of remaining gas by local selective condensation of the sterilization agent is further advantaged. The example according to FIG. 2, in which the admittance openings 32 are located in the lower corners of the outside case 30, a positioning of the port 28 in the upper area of the inside volume is advantageous on the basis of these criteria.

Figure 3:
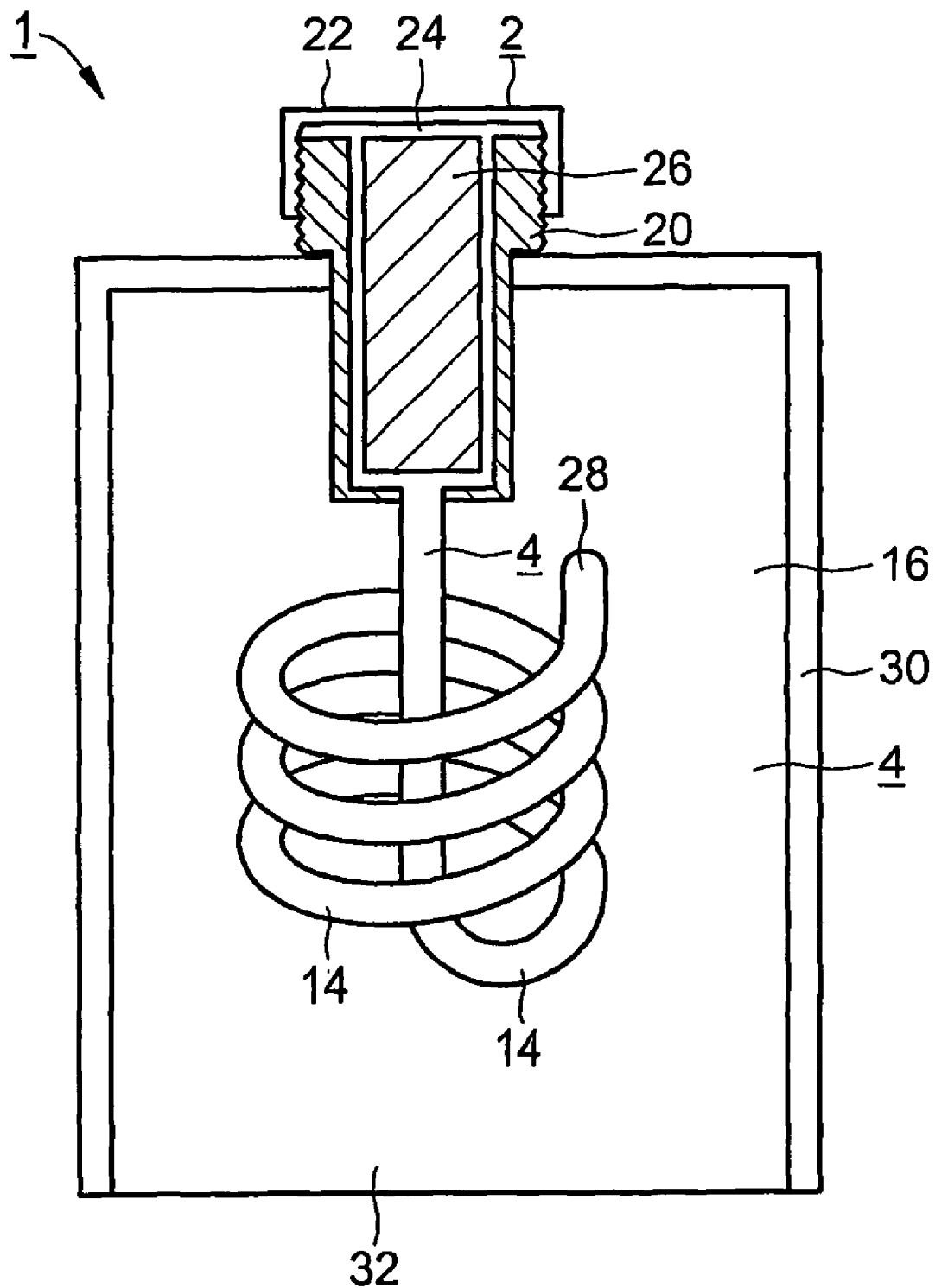
Figure 4:
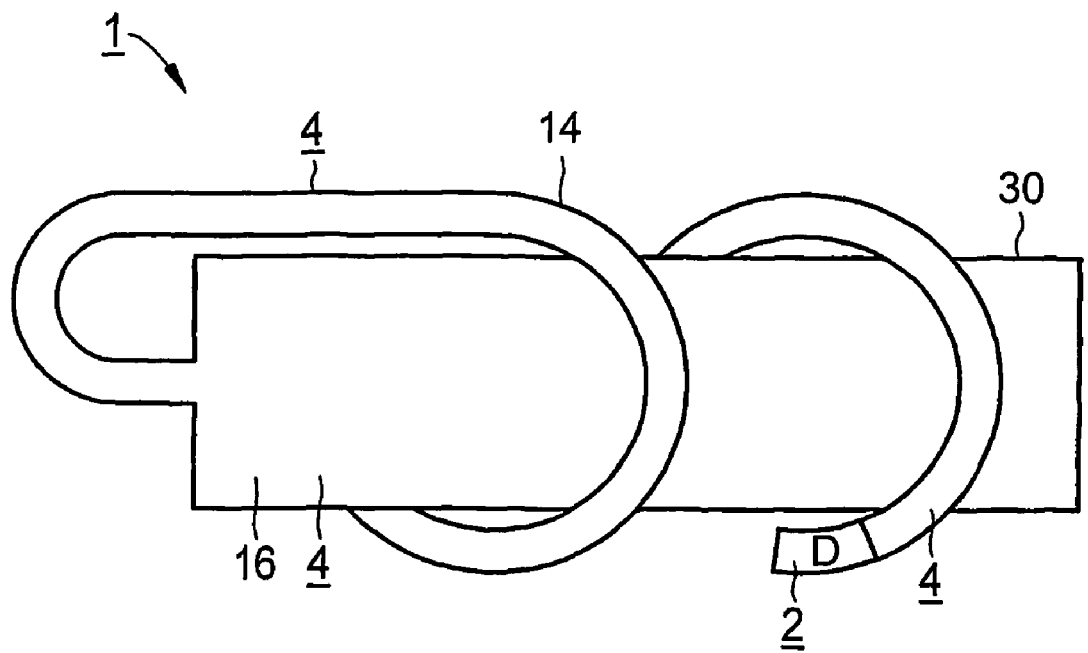
Figure 5:
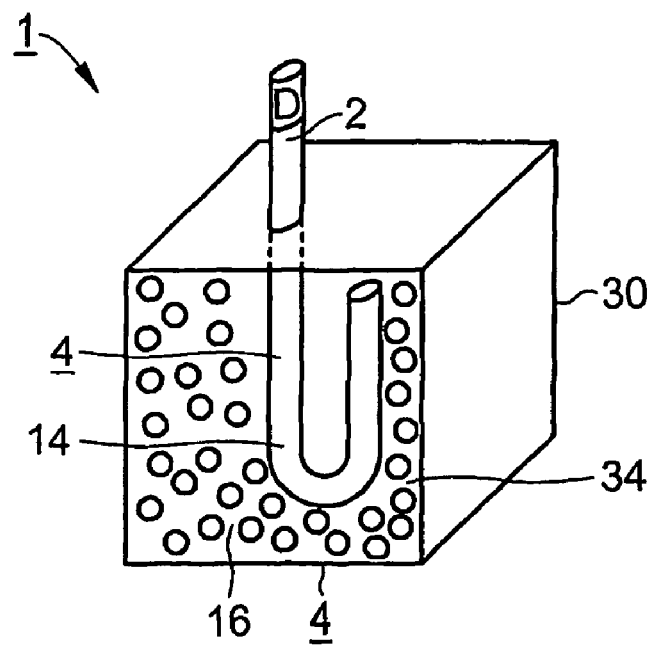

Alternative examples for the test device 1 are pictured schematically in the FIGS. 3-5. In test device 1 according to FIG. 3 the first stage 14 of the gas-collection-volume 4 is nested inside the second stage 16 of the gas-collection-volume 4. In this case, the test device 1 is designed as an especially compact construction for a very high verification sensitivity. In order to produce a comparably long channel of the first stage 14, which is advantageous to achieve an especially high verification sensitivity, at a compact construction, the first stage 14 in this example is designed as a helix inside the outside case 30, which surrounds the second stage 16. In this case the admittance opening 32 is the complete open bottom area of the outside case 30. With regard to the mentioned criteria port 28 has to be positioned near the cap area of the outside case 30.

In test device 1 according to FIG. 4 the first stage 14 of the gas-collection-volume 4 is not arranged inside, but outside the second stage 16 and positioned around the outside case 30 of the second stage 16 like a helix. At a suitable wall thickness of the outside case 30, the first stage 14 can be integrated completely into the outside wall of that example.

In the example according to FIG. 5 the test device 1 shows an essentially box-shaped outside case 30 to surround the gas-collection-volume 4. In this case the first essentially u-shaped stage is almost completely placed inside the space of the second stage 16. The second stage 16 of the test device 1 is furthermore filled with porous material 34, particularly with cellulose, cotton, glass-, mineral- or metal-wool.

LIST OF REFERENCE SYMBOLS 1 test device
2 detector
4 gas-collection-volume
6 end port
8 double arrow
12,14,16 stage
20 detector bushing
21 cap
24 detector volume
26 indicator
28 port
30 outside case
32 admittance opening
34 porous material

What is claimed is:

1. A test device comprising:
   a detector volume housing an indicator; and
   a gas-collection-volume connecting the detector volume to a sterilization chamber, wherein the gas-collection volume includes multiple stages arranged longitudinally such that a cross sectional area and a volume of each stage decrease between neighboring stages towards a direction of the detector volume, and wherein a cross-sectional area of each stage is constant over a predetermined longitudinal distance.

2. The test device as recited in claim 1, wherein the cross sectional area between the neighboring stages decreases towards the direction of the detector volume by at least 50%.

3. The test device as recited in claim 2, wherein the cross sectional area between the neighboring stages decreases towards the direction of the detector volume by more than 75%.

4. The test device as recited in claim 1, wherein the cross sectional area of the stage of the gas-collection volume directly adjacent to the detector volume is approximately 1 to 200 mm$^2$.

5. The test device as recited in claim 1, wherein the stage of the gas-collection volume directly adjacent to the detector volume has a channel length of at least 10 cm.

6. The test device as recited in claim 5, wherein the channel length is approximately 30 to 100 cm.

7. The test device as recited in claim 1, wherein a first stage of the gas-collection-volume is disposed within a second stage of the gas-collection-volume.

8. The test device as recited in claim 7, wherein the second stage is formed by an outside case enclosing the first stage.

9. The test device as recited in claim 7, wherein the first stage is built around an outside case forming the second stage.

10. The test device as recited in claim 1, wherein at least one stage is filled with porous material.

11. The test device as recited in claim 1, wherein the detector volume is approximately 100 µl to 500 µl.

12. The test device as recited in claim 1, wherein the indicator includes one of a chemical and a biological indicator.

13. The test device as recited in claim 1, wherein the test device is configured to test the penetration characteristics of a sterilization agent.

* * * * *